(12) United States Patent
Betz et al.

(10) Patent No.: US 6,533,791 B1
(45) Date of Patent: Mar. 18, 2003

(54) INSTRUMENT SYSTEM FOR THE OPERATIVE CORRECTION OF VERTEBRAL DISPLACEMENTS

(75) Inventors: Augustin Betz, Reichenau (DE); Jürgen Klein, Weikersheim (DE); Helmut Oexle, Radolfzell-Güttingen (DE); Lutz Todt, Konstanz-Dettingen (DE)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/554,039
(22) PCT Filed: Nov. 13, 1998
(86) PCT No.: PCT/EP98/07281
§ 371 (c)(1), (2), (4) Date: May 8, 2000
(87) PCT Pub. No.: WO99/25253
PCT Pub. Date: May 27, 1999

(30) Foreign Application Priority Data

Nov. 13, 1997 (DE) .......................... 197 50 382

(51) Int. Cl.⁷ .......................... A61F 2/44; A61B 17/70
(52) U.S. Cl. .......................... 606/99; 623/17.16; 606/61
(58) Field of Search .......................... 623/17.11–17.16; 606/73, 61, 72, 99; 411/385

(56) References Cited

U.S. PATENT DOCUMENTS

| | | | |
|---|---|---|---|
| 3,486,505 A | 12/1969 | Morrison | |
| 4,478,546 A | * 10/1984 | Mercer | 411/385 |
| 4,863,476 A | * 9/1989 | Shepperd | 623/17.15 |
| 5,431,658 A | 7/1995 | Moskovich | |
| 5,554,191 A | * 9/1996 | Lahille et al. | 623/17.11 |
| 5,599,279 A | 2/1997 | Slotman | |
| 5,632,748 A | * 5/1997 | Beck et al. | 606/72 |
| 5,720,748 A | * 2/1998 | Kuslich et al. | 606/80 |
| 5,865,848 A | * 2/1999 | Baker | 623/17.15 |

FOREIGN PATENT DOCUMENTS

| | | |
|---|---|---|
| DE | 4416605 C1 | 6/1995 |
| EP | 0077159 A1 | 4/1983 |
| EP | 0796593 A2 | 9/1997 |

* cited by examiner

Primary Examiner—Bruce Snow
Assistant Examiner—Brian E. Pellegrino

(57) ABSTRACT

An instrument system for the operative correction of vertebral displacements and for the stabilizing of repositioned vertebral bodies is described which is characterized by correction and support devices which are formed in two parts and which are displaceable in the axial direction guided relative to one another by means of an integrated setting member, as well as by interim spacers which are adapted in their spacer dimensions to the respective correction and support devices and by perforated hollow cylinder implants which are provided with outwardly lying fixing members and which are replaceable by the correction and support devices in repositioned vertebral bodies.

12 Claims, 4 Drawing Sheets

PRIOR ART

INSTRUMENT SYSTEM FOR THE OPERATIVE CORRECTION OF VERTEBRAL DISPLACEMENTS

BACKGROUND OF THE INVENTION

1. Field of the Invention

The invention relates to an instrument system for the operative correction of vertebral displacements and for the stabilizing of repositioned vertebral bodies.

2. Description of the Prior Art

In spinal column surgery it is known, for the stabilizing of lumbar spinal column segments, to use different implants and to fix the relative position of the vertebral bodies by means of these implants after a prior repositioning of the vertebral bodies. The erecting of the intervertebral space and the introduction of the required implants from the anterior is also already possible through laparoscopic operations. Since in operations of this kind not only must the distance between the vertebral bodies, which was reduced through the destruction of the intervertebral disc and which is possibly no longer even present, be restored, but vertebral bodies which are displaced relative to one another must also be brought back into their at least approximate intended position. Thus, it is necessary to make available to the surgeon an instrument system or assembly of instruments which on the one hand facilitates carrying out these difficult operations and on the other hand ensures that the danger of damage to nerve strands which exists in this critical spinal column region is largely excluded. In addition this instrument system must be suitable for carrying out laparoscopic operations in order to avoid through a minimally invasive approach from anterior the large, stressful intervention for the patient which is unavoidable in an open spinal column operation.

SUMMARY OF THE INVENTION

The object of the invention is therefore to create an instrument system of the initially named kind which can be used in particular in the framework of minimally invasive spinal column operations and which enables a sensitive and reliable repositioning of vertebral bodies with a subsequent exact positioning of implants which can be fixed in a simple manner, which can be anchored permanently in the bone of the adjacent vertebral body and which ensure the required stabilizing of the spinal column segments.

This object is substantially satisfied in accordance with the invention by correction and support devices which are formed in two parts and which are displaceable in the axial direction guided relative to one another by means of an integrated setting member, as well as by interim spacers which are adapted in their spacer dimensions to the respective correction and support devices and by perforated hollow cylinder implants which are provided with outwardly lying fixing members and which are replaceable by the correction and support devices in repositioned vertebral bodies.

The correction and support devices, which form the essential part of this instrument system, have a special importance in the framework of this instrument system. By means of these correction and support devices, which are introduced into the intervertebral disc space and in this are fixed with their one part at the one vertebral body and with their other part at the other vertebral body after the restoration of the intervertebral disc height, which is realized through the alternative introduction of spacers of increasing sizes, it is possible by means of relative displacing of the two parts to carry out the respective required repositioning sensitively and exactly. In this, two correction and support devices of this kind are introduced into the intervertebral disc space at least essentially centrally symmetrically, with it being possible to carry out the repositioning in a plurality of individual steps. Also, a reliable anchoring with the vertebral bodies which withstands the arising displacement forces is provided and the maintaining of the vertebral spacing is ensured at any time of the operation.

A preferred embodiment of the correction and support device which is intended for the introduction into an intervertebral disc space and which also represents an autonomous invention subject matter independently of the further constituents of the instrument system is characterized in that it comprises an upper and a lower carrier part; in that both carrier parts are provided at the outer side with elements for anchoring in the bordering vertebral bodies, in particular in the base and cover plates of these vertebral bodies; in that the two carrier parts are guided in a form-fitted manner with respect to one another at least in the direction of their mutual displaceability; and in that the integrated setting member consists of a setting screw which extends in the axial direction of the correction and support device, which is rotationally and axially fixedly journalled in a carrier part and which is in threaded engagement with the other carrier part.

In a special embodiment the correction and support device is formed in the shape of an approximately centrally divided cylindrical screw with a cylindrical head part which is formed at the actuation side, with the setting screw being rotatably journalled in one-half of the head part and being accessible for the actuation at the outwardly lying end surface of the head part and with the screw part halves which slide along one another being guided in a form-fitted manner with respect to one another via coupling elements.

In this way on the one hand an effortless and sensitive relative displacing of the two screw part halves is ensured and on the other hand it is ensured that the direction of the acting force is precisely predetermined by the form-fitted connection via the coupling elements and no disturbing and possibly dangerous rotation of the correction and support device as a whole can arise.

The coupling between the two screw part halves preferably takes place via a dovetail connection, and the two screw part halves have at the outer sides a cutting thread which is complementary to a through-going thread in a predetermined relative position. The cutting thread ensures a reliable anchoring of the screw part halves in the base and cover plates or the bone of the vertebral bodies which are to be displaced with respect to the one another respectively, which also enables the transmission of large forces and has the additional advantage that the cut thread can be used after the successive removal of the two correction and support devices which are used in an operation for the cylindrical implant, which is provided with a corresponding outer thread and which can be turned into the pre-cut thread. In this the flank heights of the cutting thread are preferably larger and the flank angles of the cutting thread are preferably smaller than the flank heights and the flank angles respectively of the cylinder implants, which are provided with an outer thread of the same pitch, through which a positioning of the implants can be achieved with large clamping and holding forces being achieved at the same time.

The cylindrically formed head part of the correction and support devices is provided at the end surface sides with coupling cut-outs and/or coupling extensions for an actuating member as well as with a threaded bore for connecting with the actuating member. A sleeve arrangement with a corresponding turning handle is preferably used as an actuating member, through which an actuation bar which can be coupled to the setting screw is passed. In this all parts are dimensioned and designed in such a manner that they can be introduced and handled through trocars.

The two screw thread halves have a different length in the axial direction, with it being possible for an edge-less protective plate to be molded on at the screw part end which faces away from and is more remote from the head part.

In accordance with a further embodiment of the invention the two carrier parts, which are displaceable relative to one another, are releasably coupled to areal, in particular plate-like, elements, which in turn can be fixed via projections, teeth and the like to the cover plates of the bordering vertebral bodies in the form of implants; i.e. these plate-like elements remain in the intervertebral disc space after the removal of the correction and support devices and the introduced implants are then supported at these plate-like elements. The implants, which preferably consist of hollow titanium screws, are filled with spongiosa, so that following the primary mechanical stability which is achieved after an operation the final stabilizing can take place after the growing through of the bone, for which the mentioned plate-like elements are designed to be perforated.

To be further mentioned is that a spreading arrangement can be provided between the two carrier parts of the correction and support device which can be actuated from the direction of the end surface of the head part and which can be used at least partly to achieve the required traction of the respective intervertebral disc space when the mutual guiding of the two carrier parts is correspondingly designed.

DETAILED DESCRIPTION OF SPECIFIC EXEMPLARY EMBODIMENTS

Figure 1:
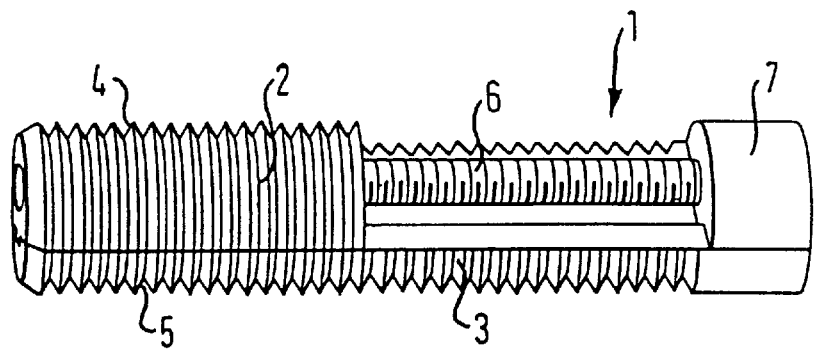
FIG. 1 is a perspective side view of a correction and support device in accordance with the invention.

The correction and support device 1 in accordance with FIG. 1 consists substantially of a screw which is separated in the axial plane and which has an upper screw part or carrier part 2 respectively and a lower screw part or carrier part 3 respectively, with the lower carrier part 3 being provided at the end face with a cylindrical head part 7 or, respectively, being formed together with the latter from uniform material.

At the outer side the carrier parts 2, 3 are provided with a screw thread which is formed as a cutting thread 4, 5, with the thread flanks, which serve as anchoring elements forming a thread with a through-going thread path when the two carrier parts 2, 3 are correspondingly mutually aligned.

The two carrier parts 2, 3 are guided with respect to one another via a form-fitted coupling axially and radially to one another and they are displaceable relative to one another by means of a setting member 6 which is executed as a screw, with it being possible to handle this setting member 6 from the direction of the end surface of the head part.

Figure 2:
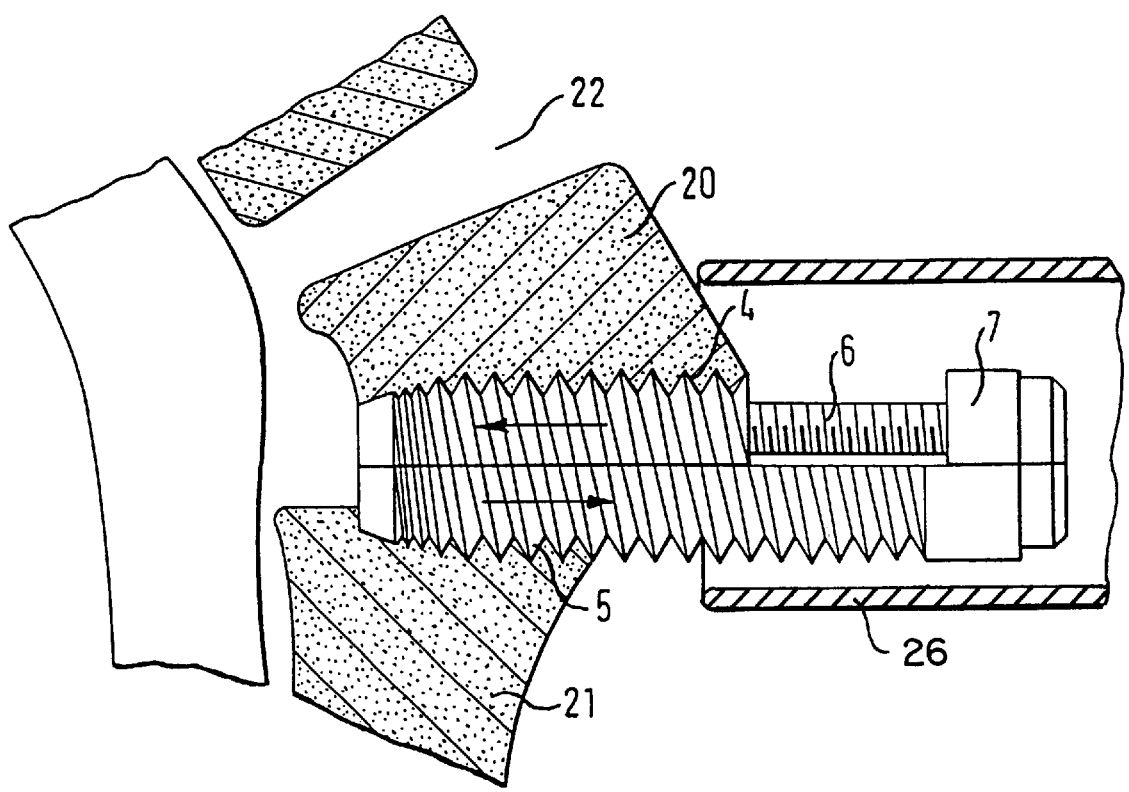
FIG. 2 is a schematic illustration for explaining the practical use of the correction and support device in accordance with FIG. 1.

FIG. 2 schematically shows a spinal column section with a plurality of vertebral bodies, with the vertebral bodies 20 and 21 being illustrated to be displaced with respect to one another in accordance with a degenerative intervertebral disc damage. These vertebral bodies 20, 21 must in the framework of an operation which is to be carried out in particular laparoscopically be brought back into a relative position which corresponds to the intended position or at least approximates the latter in order to free the afflicted patient from the pain syndrome which is connected with the faulty positioning of the vertebral bodies.

In the operating technique, which is known in principle, a traction of the intervertebral disc space 22 must as a rule first take place, with it being possible to carry out the latter through alternative insertion of spacers of increasing sizes and with the required final size for the restoration of the intervertebral disc height being pre-operatively determined. Two correction and support devices 1 are then introduced into the intervertebral disc space approximately parallel to one another and centrally symmetrically, where appropriate after corresponding pre-borings, with—as can be seen in FIG. 2—a stable and reliable anchoring of the upper and lower carrier parts being achieved in the vertebral body or in the corresponding vertebral body cover plates respectively via the cutting edge flanks of the cutting thread 4, 5. Through actuation of the setting screw 6—as shown in FIG. 2—a relative displacement of the adjacent vertebral bodies 20, 21, which are coupled in a form-fitted and force-locked manner to the two carrier parts of the correction and support device, can take place. In this the displacement procedure can be carried out extremely sensitively and in the respective possible and permissible steps, with it being important that as a result of the form-fitted guiding between the two carrier parts the displacement direction is exactly predetermined and no rotation of the correction unit can arise. The form-fitted and force-locked and thus correspondingly firm connection between the carrier parts and the vertebral bodies also provides the substantial advantage that all slipping away effects of the displacing members, which are extremely dangerous in this critical operation region and which cannot be excluded by the conventional assembly of instruments, are avoided with certainty.

When the repositioning of the vertebral body has been achieved, one of the two correction and support devices can be removed after the prior introduction of an interim spacer in the form of a sleeve having spacer lugs, and a suitable hollow cylinder implant can be introduced using the already present thread paths. The same procedure is then carried out with the second correction and support device so that after the completion of the operation the restored relative position of the adjacent vertebral bodies 20, 21 is fixed by two hollow cylinder implants, in particular in the form of hollow titanium screws which are provided with a corresponding outer thread, and the ultimate stability of the created connection can be achieved after the growing through of the bone through the hollow screw, which is filled with spongiosa.

Figure 3:
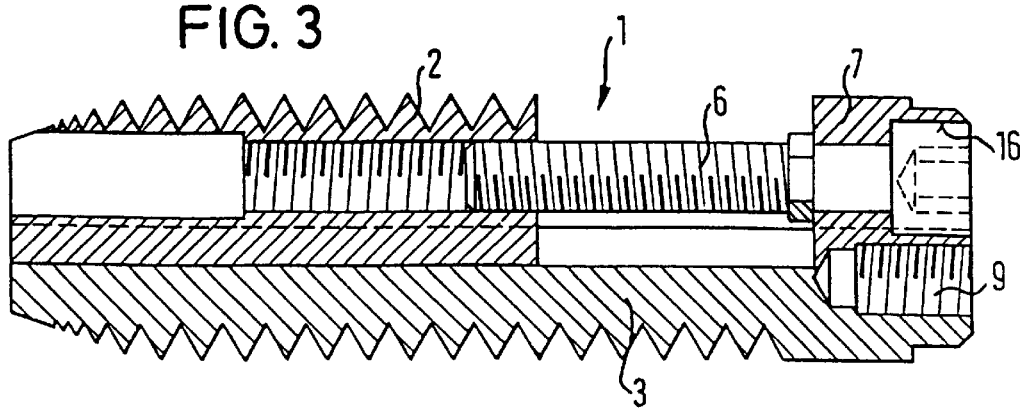
FIG. 3 is an axial section illustration of the basic elements of the correction and support device in accordance with FIG. 1.
Figure 4:
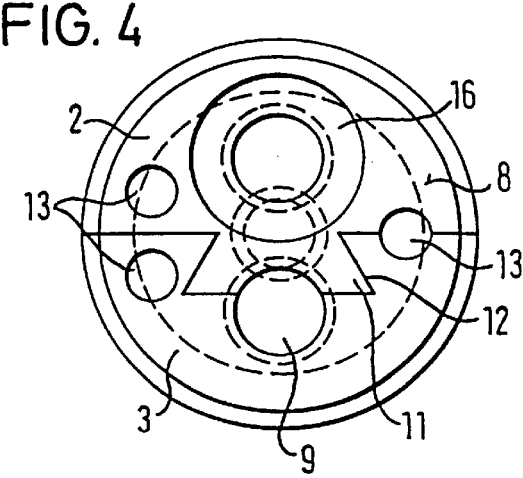
FIG. 4 is an end view of the head part of the arrangement in accordance with FIG. 3.

FIG. 3 shows a constructive embodiment of the correction and support device 1, and the end-side view in accordance with FIG. 4 shows the manner in which the correction and support device 1 can be coupled and connected to the associated actuating members.

The upper carrier part 2 slides areally on the lower carrier part 3, with it being possible for the relative displacement to take place via a setting member 6 which is formed as a screw 6 and which preferably has a fine-pitch thread. The setting member 6 is rotatably fixed in the head part in a manner which is not illustrated here in further detail, so that in a rotation of the screw head, which is arranged in a screw head reception, the respective desired relative displacement takes place. The head part 7 is furthermore provided with a threaded bore 9, via which the correction and support device 1 can be connected to a sleeve-like actuating member 17, such as is shown in FIG. 5, in a form-fitted and force-locked manner.

The relative guiding between the upper carrier part 2 and the lower carrier part 3 preferably takes place via a dovetail connection 11, 12, which can be seen in FIG. 4. Besides the cut-out 16 and the connection thread 9, mutually displaced coupling cut-outs 13 (see FIG. 8), into which corresponding pins 23 of the actuating member can engage, are provided at the end surface 8 of the head part 7 so that definite relative positions between the actuating member and the correction and support device 1 are ensured and these relative positions can also be recognized from the outside via corresponding markings.

Figure 5:
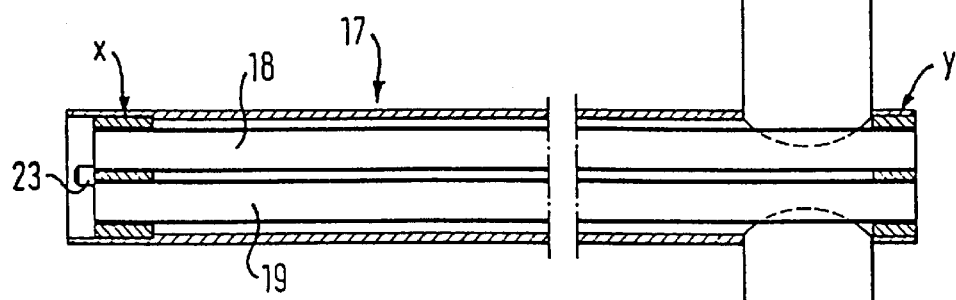
FIG. 5 is a schematic, partly sectioned illustration of an actuation sleeve arrangement for the correction and support device.
Figure 8:
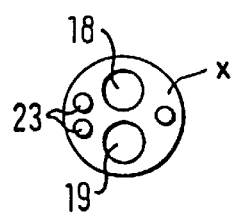
FIG. 8 is an end view of the actuation sleeve arrangement of FIG. 5.
Figure 9:
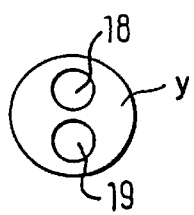
FIG. 9 is an opposite end view of the actuation sleeve arrangement of FIG. 5.

The actuating sleeve arrangement shown in FIG. 5 is adapted to the correction and support device 1 and has guiding tubes 18, 19 inside the sleeve, through which on the one hand an actuation of the setting member 6 can take place and on the other hand a fixing screw which engages into the thread 9 at the end surface side can be introduced. The sleeve 17, which is provided with a hand grip 24, is provided at both its ends with disc-like inserts x, y, as are shown in FIG. 8 and FIG. 9. The guiding tubes 18, 19 are held via these inserts and in addition the insert which is provided at the free end carries coupling pins 23 which engage into the corresponding cutouts of the correction and support device.

The grip 24 is shown rotated by 90°, and the coupling pins 23 are in alignment with the marking 25 which is provided at the grip side.

Figure 6:
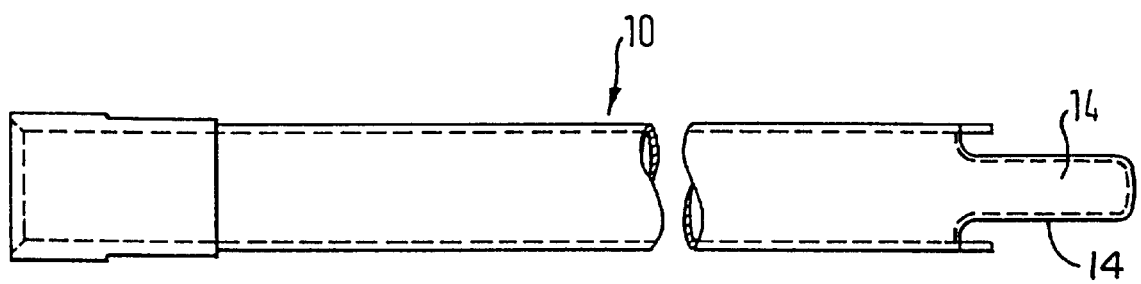
FIG. 6 is a schematic illustration of a guiding and centering sleeve with spacer function.

In order to be able to remove one of the two correction and support devices 1 in each case after completion of the repositioning of the vertebral bodies without changing the new relative position of the adjacent vertebral bodies which has been achieved by the repositioning, an interim spacer 10, such as is shown in FIG. 6, must be introduced, through which then the respective correction and support device 1 can be removed to the outside. The interim spacer 10, which has a sleeve shape, is designed in such a manner that both its spacer lugs 14, which are provided at the end sides, which lie diametrically oppositely to one another and which are adapted to the height of the respective intervertebral disc space, can be introduced at both sides of the correction and support device. After the screwing out of the correction and support device 1 the mutual spacing of the vertebral bodies is maintained by the spacer lugs 14 of the spacer 10. A relative displacement of the vertebral bodies is prevented by the other correction and support device which is still screwed in. Once the correction and support device has been removed, then the suitable hollow cylinder implant 15 is introduced through the sleeve 10 and is screwed in between the vertebral bodies using the thread which has already been cut via the correction and support device and is fixed there permanently. In a corresponding manner then the second correction and support device is replaced by a further hollow cylinder implant.

Figure 7:
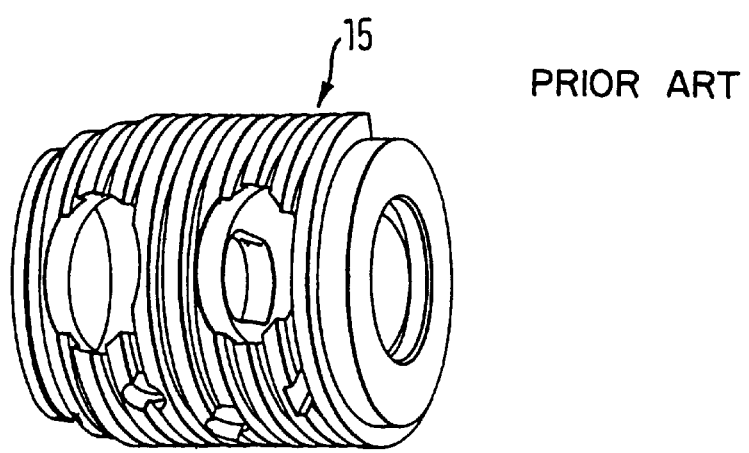
FIG. 7 is a perspective illustration of an embodiment of a perforated hollow cylinder implant.
Figure 10:
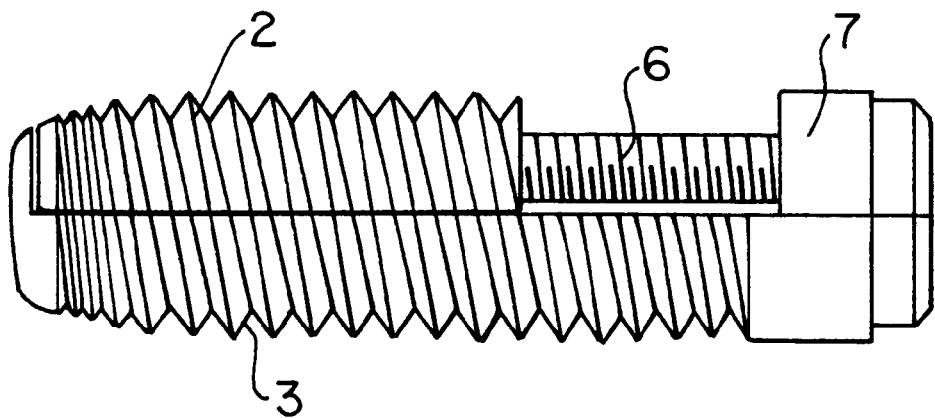
FIG. 10 is an arrangement similar to FIG. 1 with a protective disk.

An example of a hollow cylinder implant 15 of this kind is shown in FIG. 7, and it can be recognized therein that implants of this kind preferably have the shape of a perforated hollow screw which can be filled with spongiosa in order to ensure the subsequent growing through of the bone through the created structure.

Of essential importance for the invention is the correction and support device 1. All elements and units can be manipulated and handled without problem through usual trocars 26 in the carrying out of laparoscopic operations.

What is claimed is:

1. A correction and support device which has substantially the same outside diameter and pitch of an outside through-going thread as a predetermined perforated cylinder implant and which is intended to be introduced in its axial direction into a threaded hole in an intervertebral disc space of two neighbouring vertebrae, comprises an upper and a lower carrier part which both are provided for anchoring in the bordering vertebral bodies; whereby the upper and lower carrier parts are guided in a form-fitted manner with respect to one another in the axial direction for displacing one vertebra respectively to the other vertebra in axial direction; and whereby an integrated setting member consists of a setting screw which extends in the axial direction of the correction and support device, which is rotationally and axially fixedly journalled in the lower carrier part and which is in thread engagement with the upper carrier part, wherein the axial length of the upper carrier part, which is driven by the setting screw, is less than the axial length of the lower carrier part for enabling an axial displacement in both directions.

2. A correction and support device according to claim 1, wherein the upper and lower carrier parts are provided in the form of screw part halves of an in particular centrally divided, cylindrical screw with a cylindrical head part at the actuation end; whereby the setting screw is rotatably journalled in one half of the head part and is accessible at the outwardly lying end surface of the head part for actuation; and whereby the upper and lower carrier parts which slide along one another are guided in a form-fitted manner relative to one another via coupling elements.

3. A correction and support device in accordance with claim 2, wherein the coupling elements form a dovetail connection.

4. A correction and support device in accordance with claim 2 with the upper and lower carrier parts having at the outer side a cutting thread which corresponds to a through-going thread in predetermined relative positions.

5. A correction and support device in accordance with claim 4, wherein the flank height of the cutting thread is greater and the flank angles of the cutting thread are smaller than the flank heights and flank angles respectively of foreseen hollow cylinder implants, which are provided with an outer thread of the same pitch.

6. A correction and support device in accordance with claim 4, wherein a protective disc, which limits the movement of the upper carrier part that is axially shorter than the lower carrier part and which lies within the outline contour of the centrally divided cylindrical screw, is provided at the free end of the lower carrier part with outer thread.

7. A correction and support device in accordance with claim 4, wherein the upper and lower carrier parts, which are displaceable in axial direction with respect to one another are adapted to grip with their releasably coupled cutting thread into plate-like counter pieces which are fixed to a base plate and a cover plate of the bordering vertebral bodies in the form of implants.

8. A correction and support device in accordance with claim 2, wherein the setting screw has a fine thread of lesser pitch than the cylindrical screw.

9. A correction and support device in accordance with claim 1, wherein the upper carrier part is axially shorter than the lower carrier part and is coupled to the setting screw.

10. A correction and support device in accordance with claim 2, wherein a head part has coupling cut-outs or coupling extensions for an actuating member at the end surface side.

11. A correction and support device in accordance with claim 10, wherein a plurality of cut-outs for follower pins are provided in the region of the outer periphery of the end surface; and wherein the actuating member can be screwed together with a threaded bore which is likewise provided in the end surface.

12. A correction and support device in accordance with claim 1, which is axially displaceable within an interim spacer, which is formed as a centering sleeve part with axially projecting diametrically opposed spacer lugs at one end.

* * * * *